(12) United States Patent
Seo

(10) Patent No.: US 10,933,157 B2
(45) Date of Patent: Mar. 2, 2021

(54) APPARATUS FOR AIR PURIFICATION AND FRESHNESS MAINTENANCE, AND METHOD FOR CONTROLLING SAME

(71) Applicant: SEOUL VIOSYS CO., LTD, Ansan-si (KR)

(72) Inventor: Kyo Young Seo, Ansan-si (KR)

(73) Assignee: SEOUL VIOSYS CO., LTD., Ansan-si (KR)

(*) Notice: Subject to any disclaimer, the term of this patent is extended or adjusted under 35 U.S.C. 154(b) by 70 days.

(21) Appl. No.: 15/741,500

(22) PCT Filed: Jun. 30, 2016

(86) PCT No.: PCT/KR2016/007014
§ 371 (c)(1),
(2) Date: Jun. 4, 2018

(87) PCT Pub. No.: WO2017/003205
PCT Pub. Date: Jan. 5, 2017

(65) Prior Publication Data
US 2018/0272024 A1 Sep. 27, 2018

(30) Foreign Application Priority Data

Jun. 30, 2015 (KR) .................. 10-2015-0093743

(51) Int. Cl.
*A61L 9/20* (2006.01)
*F25D 17/06* (2006.01)
(Continued)

(52) U.S. Cl.
CPC ............... *A61L 9/205* (2013.01); *A23L 3/001* (2013.01); *A23L 3/3418* (2013.01); *A61L 9/20* (2013.01);
(Continued)

(58) Field of Classification Search
CPC .. F25D 2317/041; F25D 17/042; F25D 17/06; A61L 9/205
See application file for complete search history.

(56) References Cited

U.S. PATENT DOCUMENTS 4,954,465 A * 9/1990 Kawashima .............. A61L 9/20
502/5
9,803,910 B2 10/2017 Kim et al.
(Continued)

FOREIGN PATENT DOCUMENTS

CN 1330254 A 1/2002
JP 2001-009016 A 1/2001
(Continued)

OTHER PUBLICATIONS

International Search Report in International Application No. PCT/KR2016/007014, dated Sep. 12, 2016.
(Continued)

*Primary Examiner* — Cassey D Bauer
(74) *Attorney, Agent, or Firm* — Perkins Coie LLP

(57) ABSTRACT

The present invention relates to an apparatus capable of purifying air and maintaining freshness inside a refrigerator while minimizing deformation of the structure of an existing refrigerator, and a method for controlling the same. The apparatus for air purification and freshness maintenance according to the present invention is formed separately from a storage space (12) of a refrigerator (10) and is installed on a cooling passage (14) which communicates with the storage space (12) through an inlet (13) and an outlet (15), wherein a photocatalyst filter (30) is installed in the vicinity of the outlet (15) within the cooling passage (14), and a plurality of cells (32) forming an air vent are formed in the photocatalyst filter (30) in the same direction as the air flow direction within the cooling passage (14), in which a UV LED (41) for radiating ultraviolet rays toward the cells (32) of the photocatalyst filter (30) is installed.

13 Claims, 5 Drawing Sheets

(51) Int. Cl.
  F25D 29/00    (2006.01)
  B01D 46/00    (2006.01)
  B01D 53/86    (2006.01)
  F25D 17/04    (2006.01)
  F25D 23/00    (2006.01)
  A23L 3/00     (2006.01)
  A23L 3/3418   (2006.01)
  B01D 53/88    (2006.01)

(52) U.S. Cl.
  CPC ............ *B01D 46/00* (2013.01); *B01D 53/86* (2013.01); *B01D 53/8668* (2013.01); *B01D 53/885* (2013.01); *F25D 17/04* (2013.01); *F25D 17/042* (2013.01); *F25D 17/06* (2013.01); *F25D 23/00* (2013.01); *F25D 29/00* (2013.01); *A23V 2002/00* (2013.01); *A61L 2209/111* (2013.01); *A61L 2209/12* (2013.01); *A61L 2209/14* (2013.01); *B01D 2255/802* (2013.01); *B01D 2257/708* (2013.01); *B01D 2257/90* (2013.01); *B01D 2257/91* (2013.01); *B01D 2258/06* (2013.01); *B01D 2259/804* (2013.01); *F25D 2317/0417* (2013.01); *F25D 2317/0655* (2013.01); *F25D 2317/0661* (2013.01); *F25D 2700/02* (2013.01)

(56) References Cited

U.S. PATENT DOCUMENTS

| | | | | |
|---|---|---|---|---|
| 2004/0170537 A1* | 9/2004 | Hara | | A61L 9/014 422/122 |
| 2005/0217282 A1 | 10/2005 | Strohm et al. | | |
| 2008/0307818 A1* | 12/2008 | Min | | F25D 11/02 62/264 |
| 2013/0015753 A1* | 1/2013 | Son | | F25D 17/042 312/405 |
| 2013/0059047 A1 | 3/2013 | Arrigo | | |
| 2014/0245771 A1* | 9/2014 | Kim | | F25D 17/042 62/264 |
| 2015/0037217 A1* | 2/2015 | Park | | F24F 3/1603 422/121 |
| 2015/0064061 A1* | 3/2015 | Taghipour | | A61L 9/205 422/4 |
| 2015/0375187 A1* | 12/2015 | Yates | | B01J 8/008 244/118.5 |

FOREIGN PATENT DOCUMENTS

| | | |
|---|---|---|
| JP | 2001-330365 A | 11/2001 |
| JP | 2006-017358 A | 1/2006 |
| JP | 2009-181914 A | 8/2009 |
| KR | 20-2000-0021289 U | 12/2000 |
| KR | 10-2006-0106051 A | 10/2006 |
| KR | 10-2014-0101629 A | 8/2014 |
| KR | 10-2015-0006326 A | 1/2015 |

OTHER PUBLICATIONS

Supplementary European Search Report from European Patent Application No. EP16818238 dated Jan. 25, 2019, (10 pages).
English translation of Chinese Office Action from corresponding Chinese Application No. 201680038953.4 dated Jul. 30, 2019 (11 pages).
European Office Action from related European Application No. 16818238.4 dated Apr. 9, 2020 (9 pages).

* cited by examiner

APPARATUS FOR AIR PURIFICATION AND FRESHNESS MAINTENANCE, AND METHOD FOR CONTROLLING SAME

TECHNICAL FIELD

The present invention relates to an apparatus for air purification and freshness preservation and a method for controlling the same, and, more particularly, to an apparatus which can purify air inside a refrigerator and preserve freshness with minimized modification to an existing refrigerator structure.

BACKGROUND ART

Air in a food storage space of a refrigerator or the like is mixed with odors of foods, causing discomfort to a user. Considering this problem, a deodorant containing activated carbon capable of adsorbing such odors is currently being developed and sold. Such a deodorant is used in a refrigerator for a certain period of time and then discarded. The deodorant is used as a disposable product and thus has problems such as difficulty in recycling and a need for continuous replacement.

Conversely, a photocatalytic filter decomposing and deodorizing harmful gases in air using a photocatalyst material activated by UV light is recyclable and thus can be used semi-permanently.

However, since such a photocatalytic filter requires a light source providing activation energy thereto, which needs to be separated by a certain distance from the photocatalytic filter, it is not easy to dispose these components in a narrow space in a refrigerator.

In addition, since an internal space of the refrigerator has a serious level of contamination due to gases from foods, as compared with a typical indoor space, the photocatalytic filter and the light source need to be designed to maximize air purification efficiency while being as compact as possible. Therefore, in design of the photocatalytic filter and the light source, air flow path, air suction and discharge directions, filter structure, relationship between filter installation direction and air flow direction, and light source installation position need to be considered.

The odor of foods is not the only problem with using a refrigerator. When fruits or vegetables are stored in the refrigerator, the fruits or the vegetables are likely to quickly soften due to ethylene emitted therefrom. If a door of the refrigerator is frequently opened to remove ethylene from air inside the refrigerator, refrigeration efficiency can be deteriorated. Further, ethylene is not adsorbed well onto a deodorant.

In addition, floating microorganisms or bacteria can be densely present in a confined space in the refrigerator in which foods are stored. However, a deodorant cannot destroy such microorganisms or bacteria. When refrigerated foods spoil or rot due to the bacteria or microorganisms, there is a risk of stomach ache or food poisoning.

Further, harmful gases (e.g. petroleum-based aromatic compounds) eluted from a synthetic resin of an inner wall of a new refrigerator are likely to remain in a sealed space in the refrigerator for several years.

Such problems related to the air inside a typical refrigerator cannot be overcome using an air freshener or a deodorant.

Conventionally, in order to solve these problems, there has been proposed a plasma-based disinfection and deodorization technique, a method of using a carbon dioxide generator, or the like. However, these methods have neither been applied in practical use nor commercialized due to poor effects thereof.

DISCLOSURE

Technical Problem

Embodiments of the present invention have been conceived to solve such a problem in the art, and one aspect of the present invention is to provide a purification apparatus which can provide both deodorization of an internal space of a refrigerator and preservation of freshness of vegetables or fruits using a photocatalytic filter and a light source with minimized modification to an existing refrigerator structure, while providing both sterilization and removal of harmful gases.

It is another aspect of the present invention to provide an apparatus for air purification and freshness preservation, which can supply the freshest air to a storage space of a refrigerator.

It is a further aspect of the present invention to provide a method of disposing a photocatalytic filter and a light source such that resistance to airflow in a cooling channel can be minimized.

It is yet another aspect of the present invention to provide a structure capable of inhibiting propagation of bacteria in an evaporator used for cooling.

It is yet another aspect of the present invention to provide a method of controlling a purification apparatus, which allows air inside a refrigerator to remain purified in the most efficient manner.

Technical Solution

In accordance with one aspect of the present invention, there is provided an apparatus for air purification and freshness preservation which is installed in a cooling channel 14 formed separately from a storage space 12 of a refrigerator 10 and communicating with the storage space 12 through an inlet 13 and an outlet 15, the apparatus including: a photocatalytic filter 30 disposed in the vicinity of the outlet 15 of the cooling channel 14, the photocatalytic filter 30 being formed with a plurality of cells 32 constituting vent holes in an air flow direction in the cooling channel 14; and a UV LED 41 disposed in the cooling channel 14 to emit UV light toward the cells 32 of the photocatalytic filter 30.

An air discharge direction through the outlet 15 may be substantially perpendicular to a direction in which the vent holes of the photocatalytic filter 30 extend.

The UV LED 41 may be mounted on a substrate 42 disposed on an inner wall of the cooling channel 14.

The cooling channel 14 may be provided with a fan 20 forcing air to flow and an evaporator 22 cooling the flowing air, and the photocatalytic filter 30 and the UV LED 41 may be disposed downstream of the evaporator 22 in the cooling channel.

The evaporator 22 may be disposed opposite the UV LED 41 with the photocatalytic filter 30 interposed therebetween.

The photocatalytic filter 30 may be obtained by coating a surface of a base 31 with a photocatalytic material, the base having a generally cuboid shape and including a plurality of cells 32 vertically formed therethrough to allow air to pass therethrough.

In accordance with another aspect of the present invention, there is provided an apparatus for air purification and freshness preservation which is installed on a drawer 16 disposed in a storage space 12 of a refrigerator 10 and on an inner wall of the storage space 12 facing the drawer 16, the apparatus including: pores 17 formed through a wall of the drawer 16 to allow air to flow into or out of the drawer; a photocatalyst material disposed on an outer surface of the wall of the drawer with the pores 17 formed therethrough; and a UV LED 41 disposed on the inner wall of the storage space 12 to irradiate the photocatalyst material with UV light.

The apparatus may further include: a light guide plate 45 disposed on the inner wall of the storage space 12 facing the wall of the drawer with the pores 17 formed therethrough to direct light from the UV LED toward the photocatalyst material disposed on the outer surface of the wall of the drawer, wherein the UV LED 41 may emit UV light toward the light guide plate 45.

In accordance with a further aspect of the present invention, there is provided a method for controlling the apparatus for air purification and freshness preservation as set forth above, including: detecting whether a door of the refrigerator 10 is open; and shutting off power supply to the UV LED 41 when the door of the refrigerator is detected to be open.

The method may further include: turning on the UV LED 41 when the door is closed again after being detected to be open and turning off the UV LED 41 when a predetermined period of time elapses.

In the method, the fan 20 disposed in the cooling channel 14 may be operated while the UV LED 41 is turned on.

The method may further include: measuring a concentration of ethylene in air in the storage space; and turning on the UV LED 41 when the measured concentration of ethylene exceeds a reference value and turning off the UV LED 41 when a predetermined period of time elapses.

In the method, the fan 20 disposed in the cooling channel 14 may be operated while the UV LED 41 is turned on.

The method may further include: operating the evaporator 22 and the fan 20 in the cooling channel 14 when an internal temperature of the storage space rises above a reference value; and turning on the UV LED 41 while the fan 20 is operated.

The method may further include: turning off the UV LED 41 when a predetermined period of time elapses after the fan 20 is operated.

Advantageous Effects

According to the present invention, air inside a refrigerator can be semi-permanently purified and kept fresh very quickly and efficiently with minimized modification to an existing refrigerator structure.

According to the present invention, photocatalytic reaction efficiency can be greatly increased in a narrow space.

According to the present invention, propagation of bacteria or microorganisms can be suppressed very efficiently.

According to the present invention, it is possible to prevent UV light from escaping a refrigerator.

According to the present invention, air inside a refrigerator can be purified very efficiently.

The above and other aspects, features, and advantages of the present invention will become apparent from the detailed description of the following embodiments in conjunction with the accompanying drawings.

BEST MODE

Hereinafter, embodiments of the present invention will be described with reference to the accompanying drawings.

It should be understood that the present invention is not limited to the following embodiments and may be embodied in different ways, and that the embodiments are provided for complete disclosure and thorough understanding of the present invention by those skilled in the art.

First Embodiment of Apparatus for Air Purification and Freshness Preservation

Figure 1:
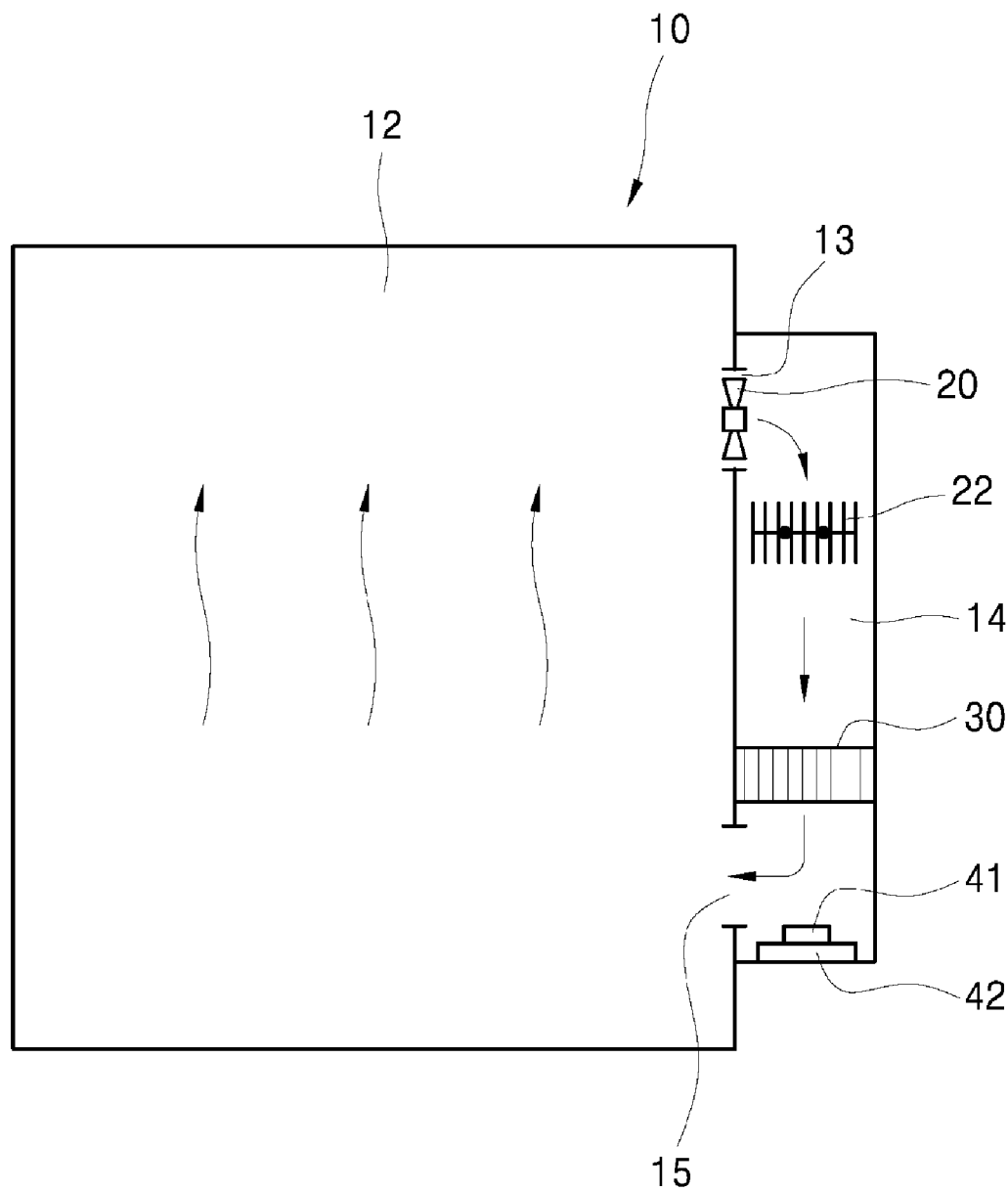
FIGS. 1 and 2 are schematic views of a refrigerator using an apparatus for air purification and freshness preservation according to a first embodiment of the present invention.
Figure 2:
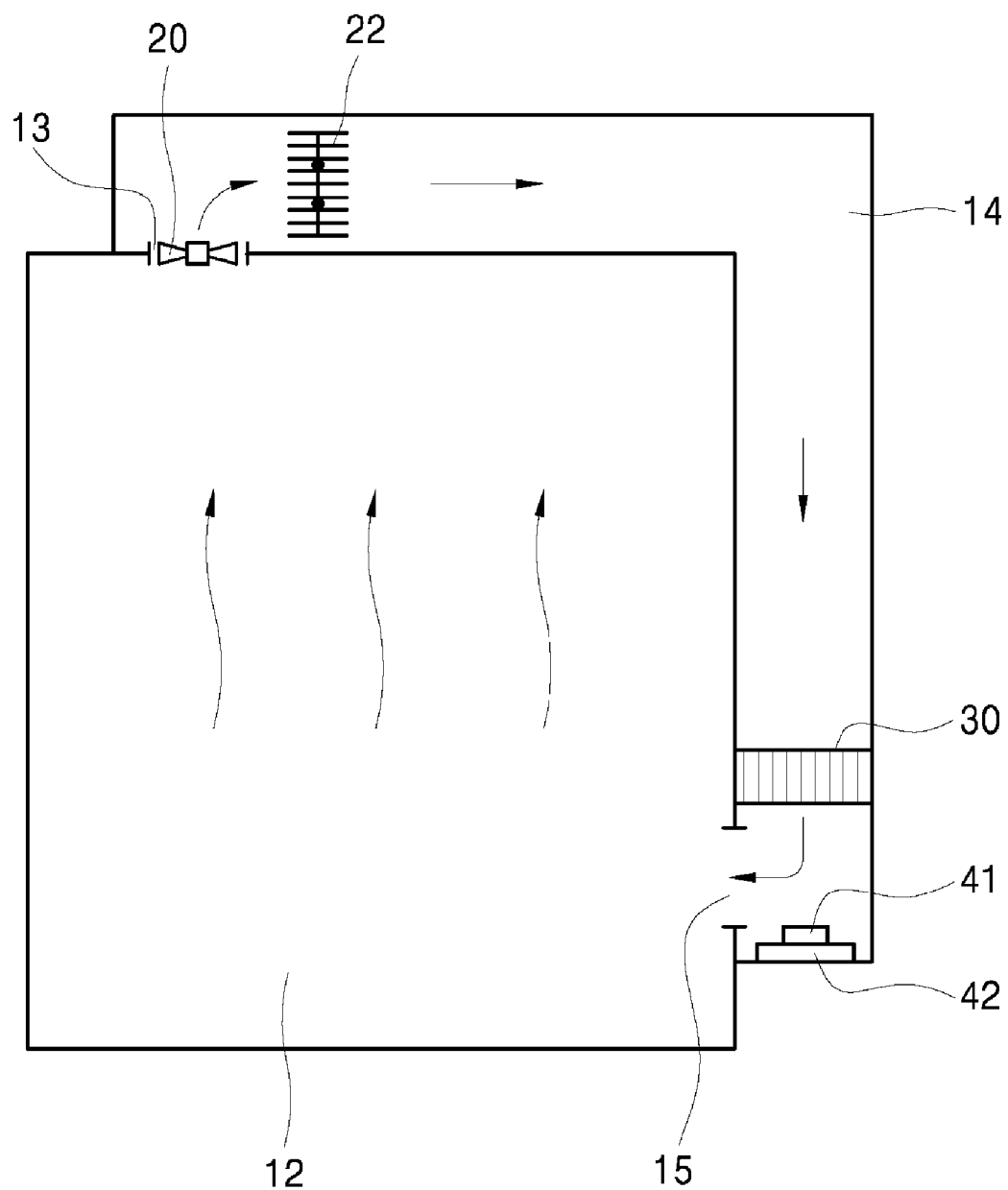
Figure 3:
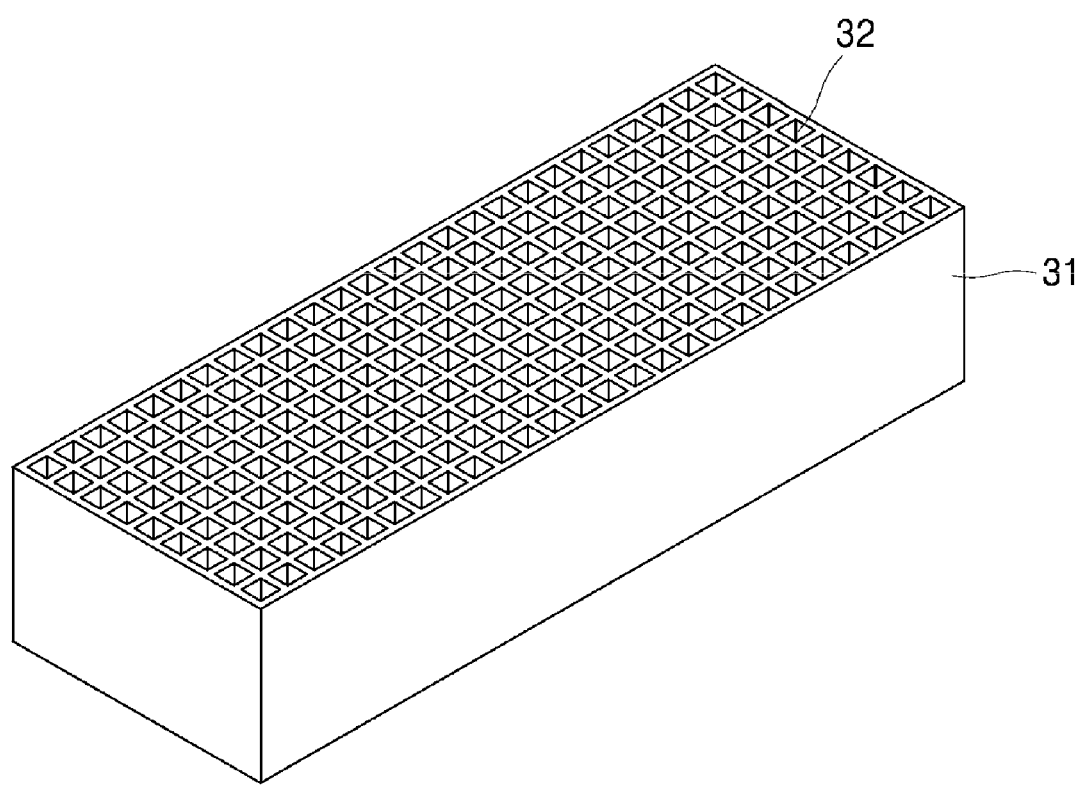
FIGS. 3 and 4 are a perspective view and plan view of a photocatalytic filter used in the apparatus for air purification and freshness preservation according to the first embodiment, respectively.
Figure 4:
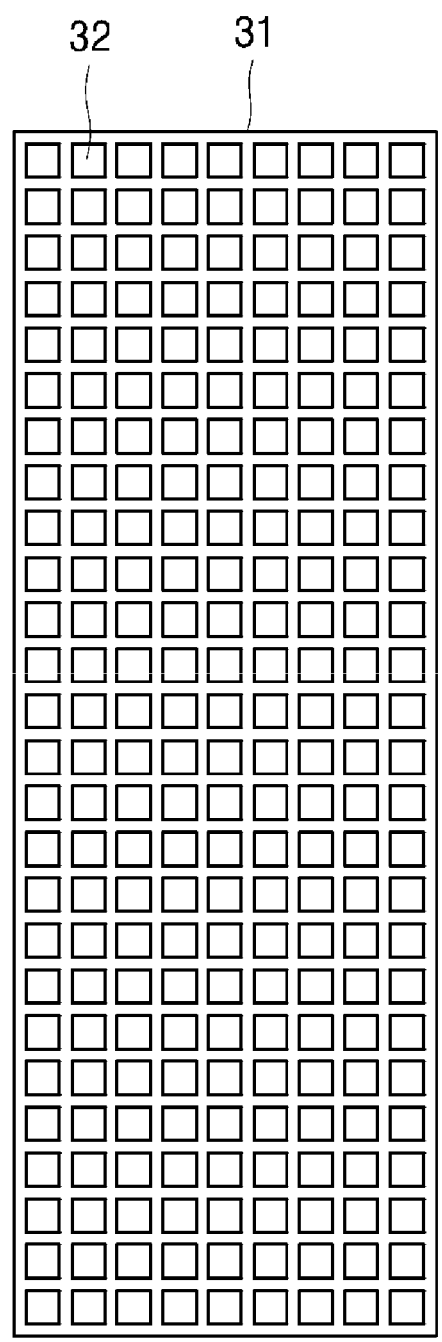

FIGS. 1 and 2 are schematic views of a refrigerator using an apparatus for air purification and freshness preservation according to a first embodiment of the present invention, and FIGS. 3 and 4 are a perspective view and plan view of a photocatalytic filter used in the apparatus for air purification and freshness preservation according to the first embodiment, respectively.

The apparatus for air purification and freshness preservation according to the present invention is installed in a refrigerator 10, as shown in the drawings. Referring to FIG. 1 or 2, the refrigerator 10 includes a storage space 12 provided with a shelf or a drawer for storage of foods (not shown) and a cooling channel 14, which is a flow path for circulating and cooling air in the storage space 12.

The cooling channel 14 is a separate space isolated from the storage space 12 and communicates with the storage space 12 through an inlet 13 and an outlet 15. The inlet 13 is an entrance through which the air in the storage space 12 is introduced into the cooling channel 14, and the outlet 15 is an exit through which the air having been introduced into the cooling channel 14 through the inlet 13 and cooled is discharged into the storage space 12. Since the air having absorbed heat of foods in the storage space 12 rises due to convection, the refrigerator 10 generally has the inlet 13 at an upper portion of the storage space 12, as shown in FIGS. 1 and 2.

The cooling channel 14 is provided therein with an evaporator 22 to perform heat exchange with air flowing through the cooling channel. In other words, the evaporator 22 absorbs heat of air flowing therearound to cool the air. In addition, the cooling channel 14 of the refrigerator 10 is provided with a fan 20 to force air to flow.

According to the present invention, a photocatalytic filter 30 and a light source 41 radiating light to activate the photocatalytic filter are disposed close to the outlet 15 of the cooling channel 14. More specifically, the photocatalytic filter 30 and the light source 41 are disposed right before the outlet of the cooling channel 14.

Air in the refrigerator sequentially circulates through the storage space 12, the inlet 13, the cooling channel 14, the outlet 15, and the storage space 12. Particularly, the storage space 12 needs to be supplied with the freshest air. Since the evaporator 22 in the cooling channel 14 is the coldest region in the refrigerator, air having absorbed moisture from foods in the storage space 12 is generally condensed on the evaporator 22. Thus, the evaporator 22 always holds moisture, and air passing through the evaporator 22 is thus likely to be contaminated. According to the present invention, the photocatalytic filter and the light source are disposed right before the outlet 15 of the cooling channel 14 to purify air just before being discharged into the storage space 12, such that the freshest air can be supplied to the storage space 12.

Generally, the inlet 13 and the outlet 15, which are passageways connecting the cooling channel 14 to the storage space 12 of the refrigerator each has a smaller cross-sectional area than the cooling channel 14. Thus, the air flowing through the cooling channel 14 has the highest pressure right before the outlet 15 of the cooling channel 14. Here, a higher pressure of air indicates a larger number of impacting gas molecules per unit area, which is directly related to photocatalytic reactivity. Since photocatalytic purification consists of brining gas into contact with radicals activated on a surface of the photocatalytic filter by photocatalytic reaction, photocatalytic efficiency can be improved by disposing the photocatalytic filter in a region in an air flow path where air pressure is highest.

Thus, when the photocatalytic filter is disposed right before the outlet 15 of the cooling channel 14 though which air is introduced into the storage space 12, the highest photocatalytic efficiency can be obtained while supplying the freshest air to the storage space 12.

Referring to FIGS. 1 to 4, the photocatalytic filter 30 has a structure in which a plurality of cells 32 vertically formed through a cuboid base 31 is arranged in a matrix and is fabricated by coating the base 31 with a photocatalytic material. The base 31 may be formed of, for example, aluminum or porous ceramics, and, as the photocatalytic material, titanium dioxide ($TiO_2$) may be used.

Although each of the cells 32 is shown as having a square cross-sectional shape, it should be understood that the present invention is not limited thereto and the cell may have any suitable shape such as a rectangular shape, an equilateral triangular shape, a right triangular shape, a regular hexagonal shape, or a combination thereof, so long as the plurality of cells can be efficiently arranged. Each of the cells may be separated by a distance of 1 mm to 4 mm, specifically 1.8 mm to 2.2 mm from the cells adjacent thereto. If the distance between the adjacent cells is excessively short, air resistance is disadvantageously increased, whereas, if the distance between the adjacent cells is excessively long, the surface area of the photocatalytic filter receiving UV light is reduced, causing deterioration in photocatalytic air purification performance.

Preferably, the height of the photocatalytic filter 10, that is, the length of an air flow path of the cell 32, ranges from 2 mm to 15 mm, more preferably 5 mm to 10 mm. If the height of the photocatalytic filter is excessively small, the photocatalytic filter is reduced in surface area and has difficulty in retaining rigidity, whereas, if the height of the photocatalytic filter is excessively large, an area of the filter which UV light cannot reach is increased, causing material waste, and air resistance is increased.

As the light source, a UV LED 41 is used. The UV LED 41 may emit UV light at a wavelength of 250 nm to 410 nm. Depending on the kind of the photocatalytic material used in the filter, the UV LED 41 may emit UV light in a wavelength range securing high activation efficiency.

Unlike a typical UV lamp, the UV LED 41 can radiate UV light in one direction and can concentrate UV light on the photocatalytic filter due to a narrow radiation angle thereof.

Referring to FIGS. 1 and 2, the UV LED 41 according to the present invention is mounted on a substrate 42, which is disposed in a direction allowing the cells 32 of the photocatalytic filter 10 to be irradiated with UV light from the UV LED.

Referring to FIGS. 1 and 2, vent holes of the photocatalytic filter 30 extend in a direction substantially perpendicular to an air discharge direction through the outlet 15. Accordingly, the size of the photocatalytic filter 30 can be maximized to correspond to a cross-sectional area of the cooling channel 14, and it is possible to prevent leakage of UV light through the outlet 15. In other words, since the outlet is formed perpendicular to an inner wall of the storage space and the cooling channel 14 is formed parallel to the inner wall of the storage space, a sufficient surface area of the photocatalytic filter can be secured by disposing the photocatalytic filter over an area corresponding to a flow cross-sectional area of the cooling channel 14. In addition, when the photocatalytic filter is disposed in the aforementioned direction, it is possible to geometrically prevent UV light emitted toward the cells, which are air flow paths of the photocatalytic filter, from leaking into the storage space through the outlet 15.

Further, when the substrate with the UV LED 41 mounted thereon is disposed on an inner wall of the cooling channel 14, as shown in FIGS. 1 and 2, it is possible to prevent the substrate 42 from interfering with the flow of air in the cooling channel 14.

A distance between the UV LED 41 and a surface of the photocatalytic filter facing the UV LED may range from 20 mm to 30 mm. If the distance therebetween is excessively long, the intensity of UV light reaching the surface of the photocatalytic filter is reduced, whereas, if the distance therebetween is excessively short, only a portion of the photocatalytic filter is irradiated with UV light.

Since the cooling channel 14 is provided with the fan 20, it is not necessary to provide a separate fan to perform photocatalytic purification and sterilization. Thus, the photocatalytic filter can be used without a separate fan by controlling the UV LED 41 to be turned on only when the fan 20 is operated or by controlling the fan 20 to be operated when the UV LED 41 needs to be turned on.

Referring to FIG. 1, the evaporator 22 is disposed opposite the UV LED 41 with the photocatalytic filter 30 interposed therebetween. In this arrangement, among UV light emitted from the UV LED 41, UV light passing through the photocatalytic filter 30 can reach the evaporator 22, thereby sterilizing the surface of the evaporator 22 on which bacteria, fungi, or microorganisms would otherwise reproduce.

Second Embodiment of Apparatus for Air Purification and Freshness Preservation

Figure 5:
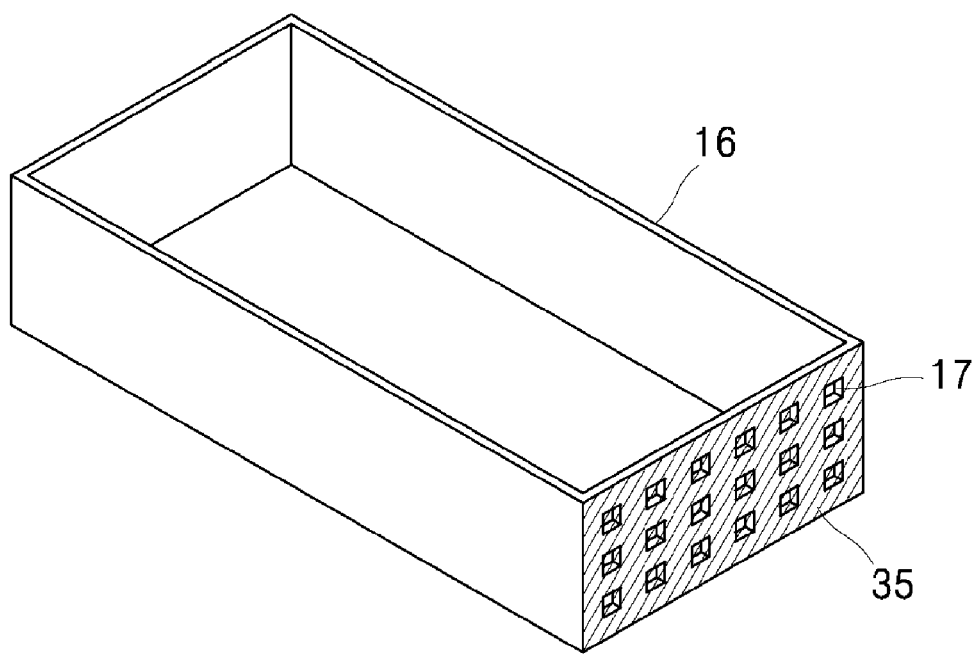
FIG. 5 is a perspective view of a photocatalyst of an apparatus for air purification and freshness preservation according to a second embodiment of the present invention
Figure 6:
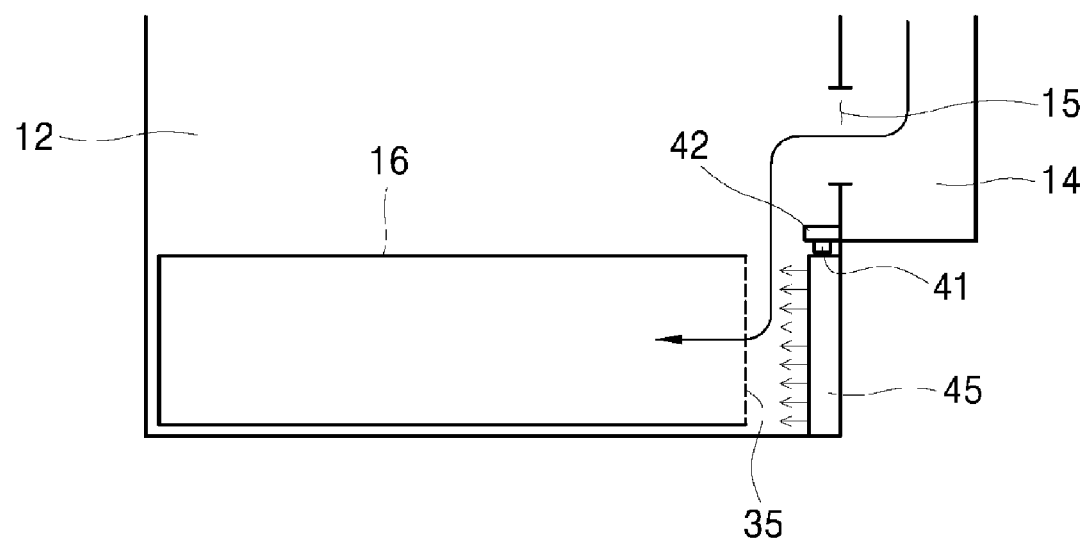
FIG. 6 is a schematic view of a refrigerator using the apparatus for air purification and freshness preservation including the photocatalyst of FIG. 5.

FIG. 5 is a perspective view of a photocatalyst of an apparatus for air purification and freshness preservation according to a second embodiment of the present invention, and FIG. 6 is a schematic view of a refrigerator using the apparatus for air purification and freshness preservation including the photocatalyst of FIG. 5.

FIG. 5 shows a drawer 16 disposed in a storage space of the refrigerator. Cold air discharged from a cooling channel 14 is introduced into the drawer 16 through pores, which are confined passages, rather than introduced directly into the drawer, such that a space inside the drawer can be prevented from being excessively cooled. Thus, the space inside the drawer is mainly used as a space for storing fruits or vegetables.

As described above, in order to provide the freshest air to the space, it is desirable that air be purified immediately before being introduced into the space and be introduced directly into the space without passing through an intervening space.

According to the present invention, a photocatalytic material is coated onto a surface of an outer wall of the drawer 16 having the pores formed therethrough to form a photocatalytic coating layer 35. The photocatalytic coating layer 35 is irradiated with UV light to induce photocatalytic purification of the air immediately before being introduced into the drawer 16.

Here, the photocatalytic coating layer 35 may be formed directly on the outer wall of the drawer 16, or may be formed by attaching a flat plate coated with a photocatalytic material to the outer wall of the drawer. It should be understood that the flat plate is configured not to block the pores 17.

In addition, a light guide plate 45 is disposed in front of the photocatalytic coating layer 35 in a face-to-face manner. Referring to FIG. 6, the light guide plate 45 is disposed on an inner wall of the storage space 12. When the UV LED 41 emits UV light toward a side surface of the light guide plate 45, the UV light is diffused into the light guide plate 45, such that surface emission of UV light to the photocatalytic coating layer 35 is achieved.

As a result, a fraction of air having been cooled through the cooling channel 14 and discharged from the cooling channel stays between the outer wall of the drawer with the pores 17 formed therethrough and the light guide plate to be purified through contact with the photocatalytic coating layer 35 formed on the outer wall of the drawer and then introduced into the drawer 16 through the pores 17.

Method for Controlling Apparatus for Air Purification and Freshness Preservation UV light in the UVC range (about 200 nm to 280 nm) is harmful to the human body. Thus, the UV LED needs to be turned off when a door of the refrigerator is open. According to the present invention, after it is detected whether the door is open, power supply to the UV LED is shut off when the door is detected to be open. Since it is the most important consideration to prevent harm to the body, when the door is detected to be open, power supply to the UV LED is shut off even upon controlling the UV LED to be turned on, which will be described below.

According to the present invention, when the door is opened and then closed, the UV LED is supplied with power for a predetermined period of time to cause photocatalytic reaction, thereby purifying air and increasing freshness. After the door is opened and closed, it is necessary to purify external air having flowed into the storage space of the refrigerator. Here, the predetermined period of time may be set such that 99% or more of harmful gases such as ethylene can be decomposed.

During the time when the UV LED is turned on, it is preferable to operate the fan 20 to increase air purification capability. Although the fan 20 is configured to cool air during operation of the evaporator 22, it is desirable that the fan also be operated during photocatalytic reaction to improve air purification efficiency.

According to the present invention, the apparatus is provided with a sensor capable of measuring the concentration of ethylene in the storage space. When the concentration of a volatile organic gas, such as ethylene, measured by the sensor exceeds a reference value, the UV LED is controlled to be turned on and then turned off after being operated for a predetermined period of time. Here, the predetermined period of time may be set such that 99% or more of harmful gases, such as ethylene, can be decomposed. During the time when the UV LED is operated, it is preferable to operate the fan 20 to improve air purification capability.

In addition, according to the present invention, when the temperature in the storage space rises above a reference value and the evaporator 22 and the fan 20 are thus operated, the UV LED may be controlled to be turned on. Power consumed for air purification can be minimized by turning on the UV LED during the time when the fan is operated to cool the air, rather than separately operating the fan only for air purification. Here, the UV LED is turned off after a period of time for which 99% or more of harmful gases in the refrigerator, such as ethylene, can be decomposed.

The aforementioned control processes may be used alone or in combination thereof.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the present invention. In addition, it should be understood that, although advantageous effects of the features of the present invention have not been explicitly described, predictable effects of the features should also be recognized.

<List of Reference Numerals>

| | |
|---|---|
| 10: refrigerator | 12: storage space |
| 13: inlet | 14: cooling channel |
| 15: outlet | 16: drawer |
| 17: pore | 20: fan |
| 22: evaporator (heat exchanger) | 30: photocatalytic filter |
| 31: base | 32: cell |
| 35: photocatalytic coating layer | 41: UV LED |
| 42: substrate | 45: light guide plate |

The invention claimed is:

1. An apparatus for air purification and freshness preservation installed in a cooling channel formed separately from a storage space of a refrigerator and communicating with the storage space through an inlet and an outlet, the apparatus comprising:
    a photocatalytic filter disposed closer to the outlet of the cooling channel than the inlet of the cooling channel, the photocatalytic filter having a plurality of cells constituting vent holes in an air flow direction in the cooling channel; and
    an ultraviolet light emitting diode (UV LED) disposed in the cooling channel to emit UV light toward the cells of the photocatalytic filter, wherein the cooling channel includes a fan forcing air to flow and an evaporator cooling the flowing air, and the photocatalytic filter and the UV LED are disposed downstream of the evaporator in the cooling channel.

2. The apparatus for air purification and freshness preservation according to claim 1, wherein the evaporator is disposed opposite the UV LED with the photocatalytic filter interposed therebetween.

3. A method for controlling an apparatus for air purification and freshness preservation installed in a cooling channel formed separately from a storage space of a refrigerator and communicating with the storage space through an inlet and an outlet, wherein the apparatus includes a photocatalytic filter disposed closer to the outlet of the cooling channel than the inlet of the cooling channel, the photocatalytic filter having a plurality of cells constituting vent holes in an air flow direction in the cooling channel; and an ultraviolet light emitting diode (UV LED) disposed in the cooling channel to emit UV light toward the cells of the photocatalytic filter, the method comprising:

detecting whether a door of the refrigerator is open; and
   shutting off power supply to the UV LED when the door of the refrigerator is detected to be open,
   wherein the cooling channel includes a fan forcing air to flow and an evaporator cooling the flowing air, and the photocatalytic filter and the UV LED are disposed downstream of the evaporator in the cooling channel.

4. The method according to claim 3, further comprising:
   turning on the UV LED when the door is closed again after being detected to be open and turning off the UV LED when a predetermined period of time elapses.

5. The method according to claim 4, wherein the fan disposed in the cooling channel is operated while the UV LED is turned on.

6. The method according to claim 3, further comprising:
   measuring a concentration of ethylene in air in the storage space; and
   turning on the UV LED when the measured concentration of ethylene exceeds a reference value and turning off the UV LED when a predetermined period of time elapses.

7. The method according to claim 6, wherein the fan disposed in the cooling channel is operated while the UV LED is turned on.

8. The method according to claim 3, further comprising:
   operating the evaporator and the fan in the cooling channel when an internal temperature of the storage space rises above a reference value; and
   turning on the UV LED while the fan is operated.

9. The method according to claim 8, further comprising:
   turning off the UV LED when a predetermined period of time elapses after the fan is operated.

10. The method according to claim 3, wherein an air discharge direction through the outlet is substantially perpendicular to a direction in which the vent holes of the photocatalytic filter extend.

11. The method according to claim 10, wherein the UV LED is mounted on a substrate disposed on an inner wall of the cooling channel.

12. The method according to claim 3, wherein the evaporator is disposed opposite the UV LED with the photocatalytic filter interposed therebetween.

13. The method according to claim 3, wherein the photocatalytic filter is obtained by coating a surface of a base with a photocatalytic material, the base having a cuboid shape and comprising a plurality of cells vertically formed therethrough to allow air to pass therethrough.

* * * * *